US011607117B2

(12) United States Patent
Jurevicius et al.

(10) Patent No.: US 11,607,117 B2
(45) Date of Patent: Mar. 21, 2023

(54) ENDOSCOPE HANDLE HOLDER WITH ANGULATION LEVER LOCK-OUT

(71) Applicant: GYRUS ACMI, INC., Redmond, WA (US)

(72) Inventors: Christine N. Jurevicius, Issaquah, WA (US); Taylor N. Tyson, Seattle, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 592 days.

(21) Appl. No.: 16/168,337

(22) Filed: Oct. 23, 2018

(65) Prior Publication Data

US 2020/0121164 A1    Apr. 23, 2020

(51) Int. Cl.
*A61B 1/005* (2006.01)
*A61B 1/00* (2006.01)
*A61M 25/01* (2006.01)

(52) U.S. Cl.
CPC .......... *A61B 1/0052* (2013.01); *A61B 1/0014* (2013.01); *A61B 1/00042* (2022.02); *A61B 1/00105* (2013.01); *A61M 25/0136* (2013.01)

(58) Field of Classification Search
CPC ............. A61M 25/0136; A61B 1/0052; A61B 1/00105; A61B 1/0014; A61B 1/00039; A61B 1/00042; A61B 1/00066
USPC ........................................................ 600/102
See application file for complete search history.

(56) References Cited

U.S. PATENT DOCUMENTS

| 5,810,712 A | 9/1998 | Dunn |
| 6,971,987 B1 | 12/2005 | Chung |
| 8,864,656 B2 | 10/2014 | Konstorum |
| 2002/0165484 A1* | 11/2002 | Bowe ................ A61M 25/0136 604/95.05 |
| 2010/0312055 A1* | 12/2010 | Konstorum ........ A61B 1/00066 600/131 |
| 2017/0143195 A1* | 5/2017 | Yee .................... A61B 1/00133 |

FOREIGN PATENT DOCUMENTS

| JP | 2001346755 A | * 11/2001 | |
| KR | 20160042225 A | * 4/2016 | |
| WO | WO-2014115068 A1 | * 7/2014 | .......... A61B 1/0057 |

OTHER PUBLICATIONS

Rk Mishra et al., Comparison of PMAT Camera Holder with Human Camera Holder, World Journal of Laparoscopic Surgery, May-Aug. 2008, pp. 1-5.
User's Manual for STEADICAM by Tiffen, p. 6 (The Pilot Vest).

* cited by examiner

*Primary Examiner* — Aaron B Fairchild
*Assistant Examiner* — Christen A. Sharpless
(74) *Attorney, Agent, or Firm* — Schwegman Lundberg & Woessner, P.A

(57) ABSTRACT

Disclosed embodiments include apparatuses for holding an endoscope handle and locking out an angulation lever of an endoscope handle. Given by way of illustration only and not of limitation, in an embodiment an illustrative apparatus includes: a frame; a support mechanism attached to the frame and configured to hold thereon an endoscope handle having an angulation lever; an attachment device configured to hold an endoscope handle in place on the support mechanism; and an angulation lever engagement mechanism configured to prevent an angulation lever of an endoscope handle from returning to a neutral position.

20 Claims, 8 Drawing Sheets

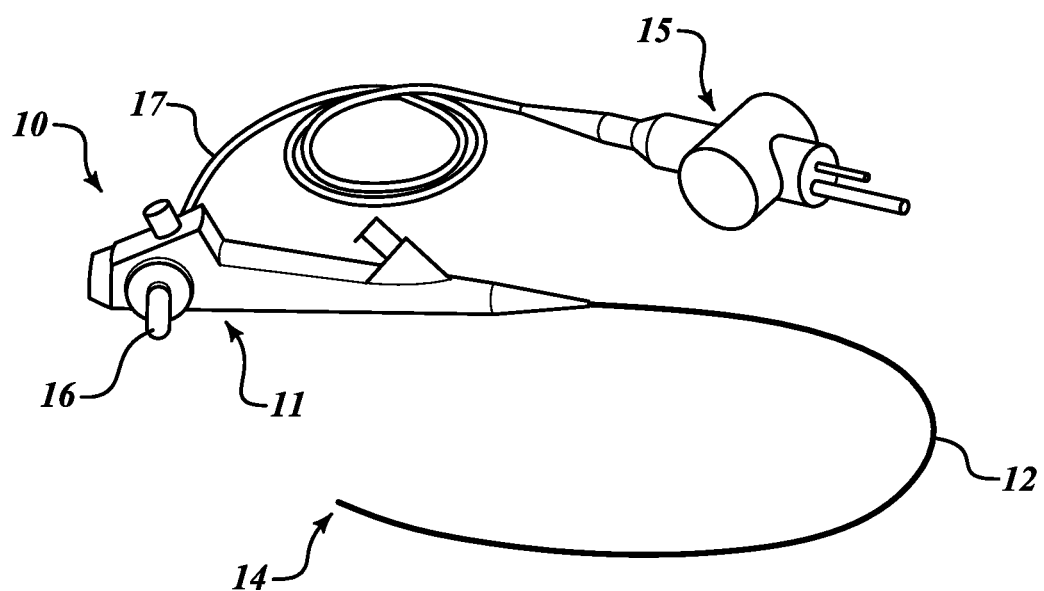
FIG.1A *(Prior Art)*

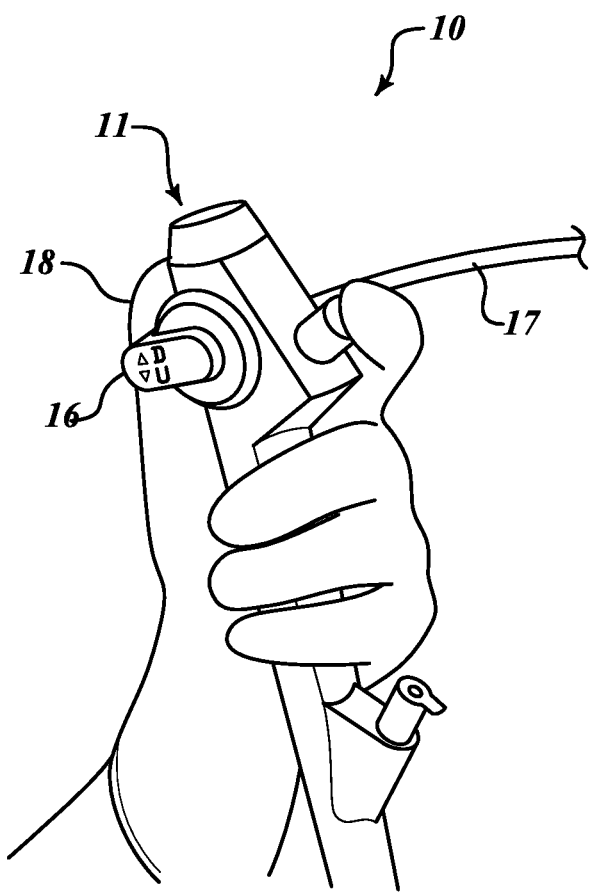
FIG. 1B *(Prior Art)*

ENDOSCOPE HANDLE HOLDER WITH ANGULATION LEVER LOCK-OUT

FIELD

The present disclosure relates to controlling an endoscope.

BACKGROUND

The statements in this section merely provide background information related to the present disclosure and may not constitute prior art.

Endoscopes are used in a variety of medical procedures that are generally referred to as endoscopy (or endoscopic procedures). Endoscopy entails insertion of a long, thin tube directly into an opening in a patient's body to perform a medical procedure at a distal tip of the tube. Such procedures may include observing an internal organ or tissue in detail, imaging a target area of tissue, performing a biopsy of a target area of tissue, and/or performing minor surgery and/or ablation on a target area of tissue.

Referring to FIGS. 1A and 1B, an endoscope 10 (such as a bronchoscope as shown in FIGS. 1A and 1B) includes an endoscope handle 11. Extending from the endoscope handle 11 is a long, thin tube 12 with a distal tip 14. A source 15 (such as a light source or an electrical power source) is operably coupled to the endoscope handle 11 via a wire bundle 17. An endoscopic procedure (such as imaging, performing a biopsy, performing minor surgery and/or ablation) is carried out by sensors or effectors (not shown) disposed at the distal tip 14.

Orientation and position of the distal tip 14 is controlled, in part, by an angulation lever 16 rotatably disposed on the endoscope handle 11. Typically, wires (not shown) within the endoscope handle 11 and the tube 12 are operably coupled to the distal tip 14 and the angulation lever 16. Rotation of the angulation lever 16 causes the wires (not shown) to move, thereby causing the distal tip 14 to deflect in response thereto. Some endoscopes 10 (such as a bronchoscope as shown in FIGS. 1A and 1B) have one angulation lever 16 and can control deflection of the distal tip 14 in one direction (such as up/down). Some other endoscopes (not shown) may have more than one angulation lever and may control deflection of the distal tip in more than one direction (such as up/down and left/right).

Conventionally, a user (such as a surgeon) holds the endoscope handle 11 in one hand and controls deflection of the distal tip 14 by positioning the angulation lever 16 with a thumb 18. In some endoscopes, the angulation lever 16 has a "return-to-neutral" feature—that is, the distal tip 14 returns to a neutral position (no deflection) if the angulation lever 16 ceases to be held in place by the user's thumb 18. Thus, during an endoscopic procedure a user must hold the endoscope handle 11 and, in addition, must hold the angulation lever 16 in place to maintain desired deflection of the distal tip 14. As a result, a user, such as a surgeon, can get tired from holding the endoscope handle 11 with the angulation lever 16 in a set position during an endoscopic procedure (which can take a long period of time).

SUMMARY

Disclosed embodiments include apparatuses for holding an endoscope handle and locking out an angulation lever of an endoscope handle.

Given by way of illustration only and not of limitation, in an embodiment an illustrative apparatus includes: a frame; a support mechanism attached to the frame and configured to hold thereon an endoscope handle having an angulation lever; an attachment device configured to hold an endoscope handle in place on the support mechanism; and an angulation lever engagement mechanism configured to prevent an angulation lever of an endoscope handle from returning to a neutral position.

In another embodiment an illustrative apparatus includes: a frame; a support mechanism attached to the frame and configured to hold thereon an endoscope handle having an angulation lever; an attachment device configured to hold an endoscope handle in place on the support mechanism; and an angulation lever engagement mechanism configured to prevent an angulation lever of an endoscope handle from returning to a neutral position, the angulation lever engagement mechanism including: an engagement member configured to engage an angulation lever of an endoscope handle at a position corresponding to a selected deflection of a distal tip of an endoscope; and a locking mechanism configured to lock the engagement member in place, wherein the locking mechanism is separate from the engagement member and is configured to hold the engagement member in place against the frame.

In another embodiment an illustrative apparatus includes: a frame; a support mechanism attached to the frame and configured to hold thereon an endoscope handle having an angulation lever; an attachment device configured to hold an endoscope handle in place on the support mechanism; and an angulation lever engagement mechanism configured to prevent travel of an angulation lever of an endoscope handle, the angulation lever engagement mechanism including: an engagement member configured to receive therein an angulation lever of an endoscope handle at a position corresponding to a selected deflection of a distal tip of an endoscope; and a locking mechanism configured to lock the engagement member in place, wherein the locking mechanism is integrated with the engagement member and is configured to frictionally engage a portion of an endoscope handle.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIG. 1A is a perspective view of a conventional endoscope;

FIG. 1B is a perspective view of a conventional endoscope handle being held by a user;

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two-digits of the figure numbers, respectively, in which the element first appears.

The following description explains, by way of illustration only and not of limitation, various embodiments of apparatuses for holding an endoscope handle and locking out an angulation lever of an endoscope handle. It will be appreciated that various disclosed embodiments may be suitable for use with various endoscopes, such as without limitation a bronchoscope as shown in FIGS. 1A and 1B. As will be explained below, various embodiments are configured to hold an endoscope handle and lock out an angulation lever of an endoscope handle by preventing the angulation lever from returning to a neutral position. As will also be explained below, various other embodiments are configured to hold an endoscope handle and lock out an angulation lever of an endoscope handle by preventing any travel of the angulation lever (in addition to preventing the angulation lever from returning to a neutral position). Thus, it will be appreciated that various disclosed embodiments may help contribute to obviating a need for a user to hold an endoscope handle and, in addition, hold an angulation lever in place to maintain desired deflection of a distal tip during an endoscopic procedure. Details will be explained below by way of illustrative, non-limiting embodiments that are set forth by way of illustration only and not of limitation.

Figure 2:
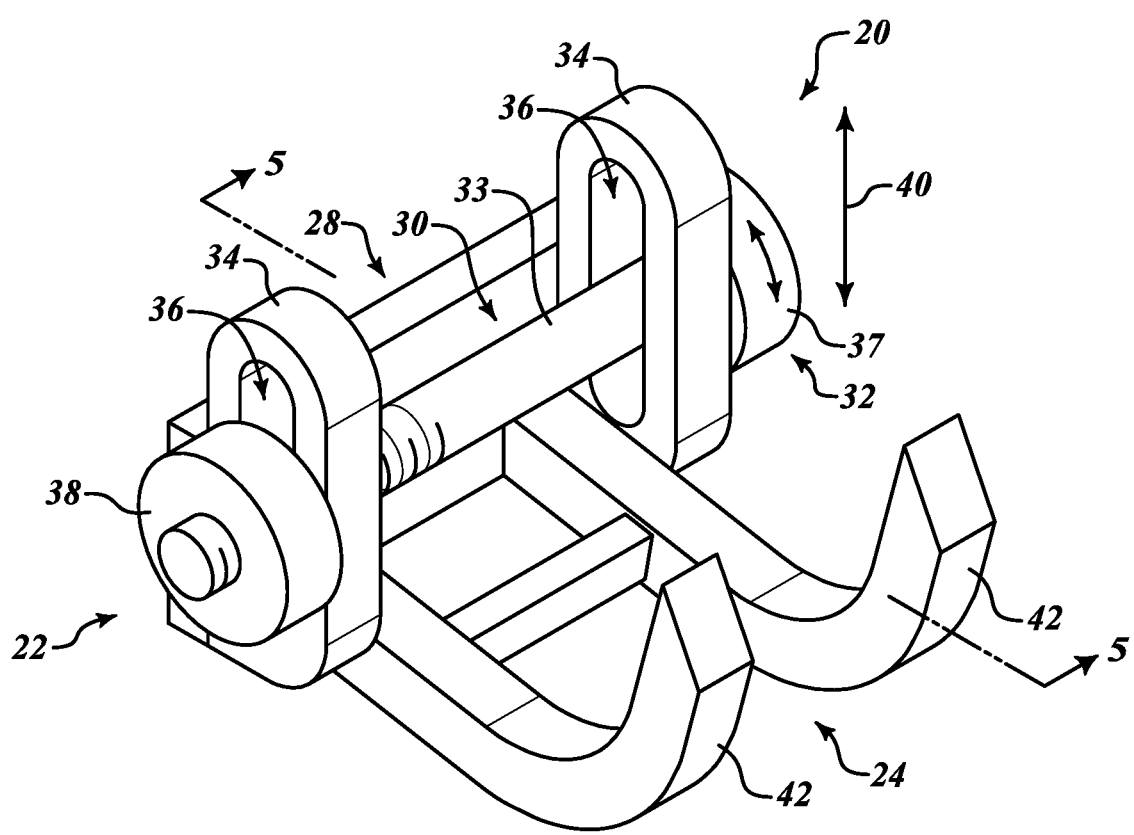
FIG. 2 is a perspective view of an illustrative apparatus for holding an endoscope handle and locking out an angulation lever of an endoscope handle.
Figure 5:
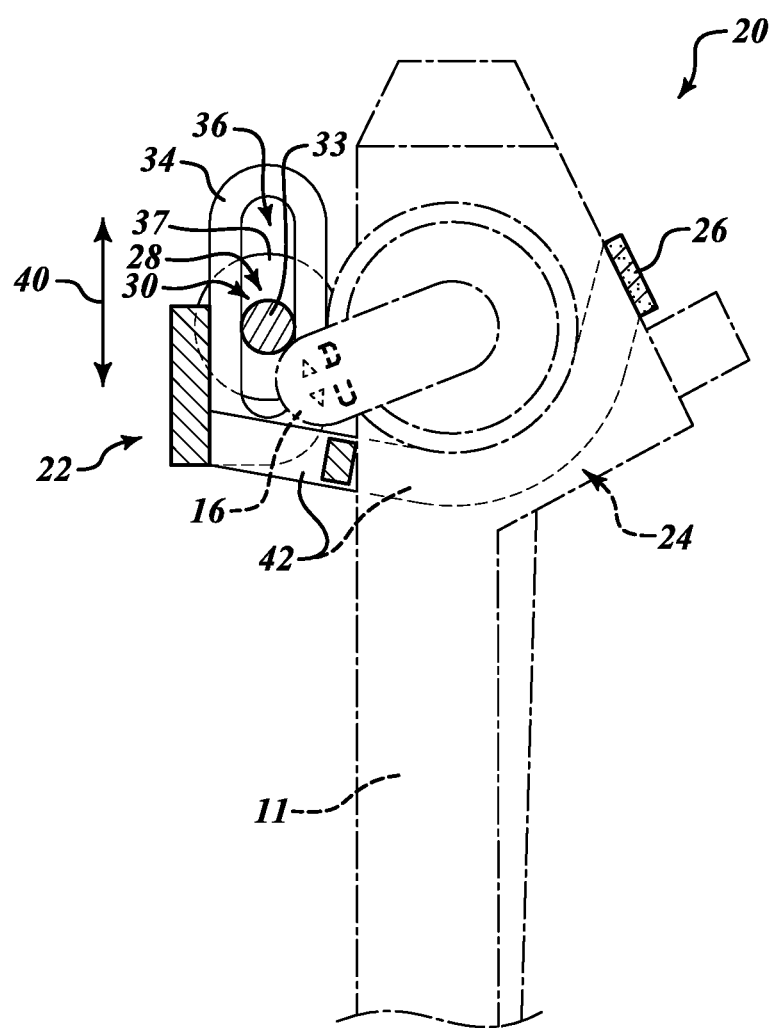
FIG. 5 is a side plan view in partial cutaway of the apparatus of FIG. 2 with an endoscope handle held thereon.

Referring now to FIGS. 2 and 5, in various non-limiting embodiments an illustrative apparatus 20 includes a frame 22. A support mechanism 24 is attached to the frame 22 and is configured to hold thereon an endoscope handle 11 (shown in phantom in FIG. 5) having an angulation lever 16 (shown in phantom in FIG. 5). An attachment device 26 is configured to hold the endoscope handle 11 in place on the support mechanism 24. An angulation lever engagement mechanism 28 is configured to prevent the angulation lever 16 from returning to a neutral position.

In various embodiments, the angulation lever engagement mechanism 28 includes an engagement member 30 that is configured to engage the angulation lever 16 at a position corresponding to a selected deflection of a distal tip (reference number 14 in FIG. 1A; not shown in FIGS. 2 and 5) of the endoscope 10. In such embodiments, the angulation lever engagement mechanism 28 also includes a locking mechanism 32 that is configured to lock the engagement member 30 in place.

In some embodiments, the engagement member 30 includes a bar member 33 that is configured to prevent the angulation lever 16 from returning to a neutral position. In some such embodiments and as shown in FIGS. 2 and 5, the bar member 33 is further configured to abut the angulation lever 16. In such embodiments, the frame 22 includes frame members 34 that each define a slot 36 therein.

In some such embodiments, the locking mechanism 32 is configured to hold the engagement member 30 in place against the frame 22. In some embodiments, the locking mechanism 32 may include a knob 37 that is tightenable against one of the frame members 34 and a stop member 38 that is attached to an end of the bar member 33.

In such embodiments, the bar member 33 slides up and down (as indicated by arrow 40) depending on the desired location of the angulation lever 16. If the angulation lever 16 is down, then the bar member 33 will be on top of the angulation lever 16. If the angulation lever 16 is up, then the bar member 33 will be below the angulation lever 16. The locking mechanism 32 is engaged to hold the bar member 33 in place. In some embodiments, the knob 37 will be tightened to draw the stop member 38 against its associated frame member 34, thereby holding the bar member 33 in place. It will be appreciated that, in such embodiments, the angulation lever engagement mechanism 28 functions as a limit stop. That is, the angulation lever 16 is prevented from returning to a neutral position but, if desired, the angulation lever 16 can be caused to travel farther away from a neutral position (thereby resulting in increased deflection of the distal tip).

In various embodiments, the support mechanism 24 may include at least two support members 42. As shown in FIGS. 2-3 and 5-7, in some embodiments the support mechanism 24 may include two support members 42, such as curved bars. It will be appreciated that the support mechanism 24 may include any number of support members 42 as desired for a particular application.

In various embodiments, the attachment device 26 may include any suitable device for holding the endoscope handle 11 onto the support mechanism 10, such as without limitation a strap, hook-and-loop fasteners, a clamp, a funnel, or the like.

Figure 3:
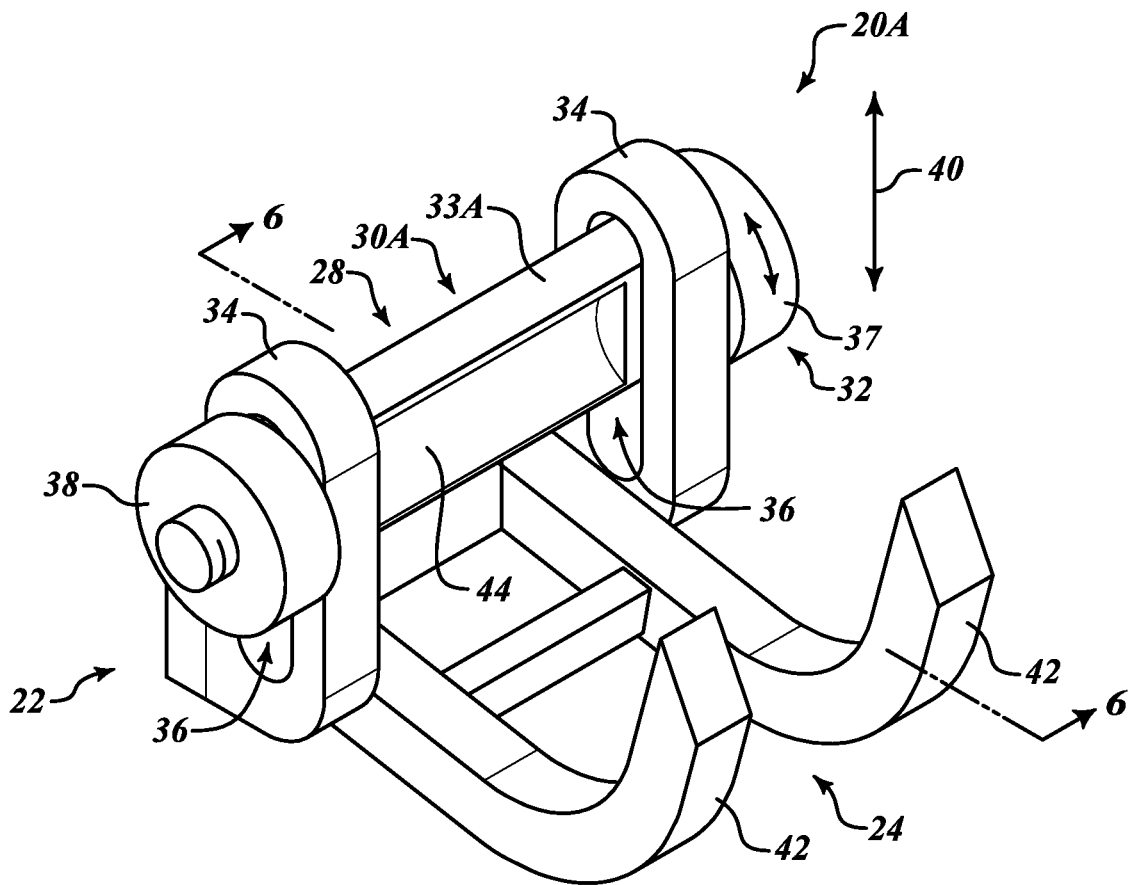
FIG. 3 is a perspective view of another illustrative apparatus for holding an endoscope handle and locking out an angulation lever of an endoscope handle.
Figure 6:
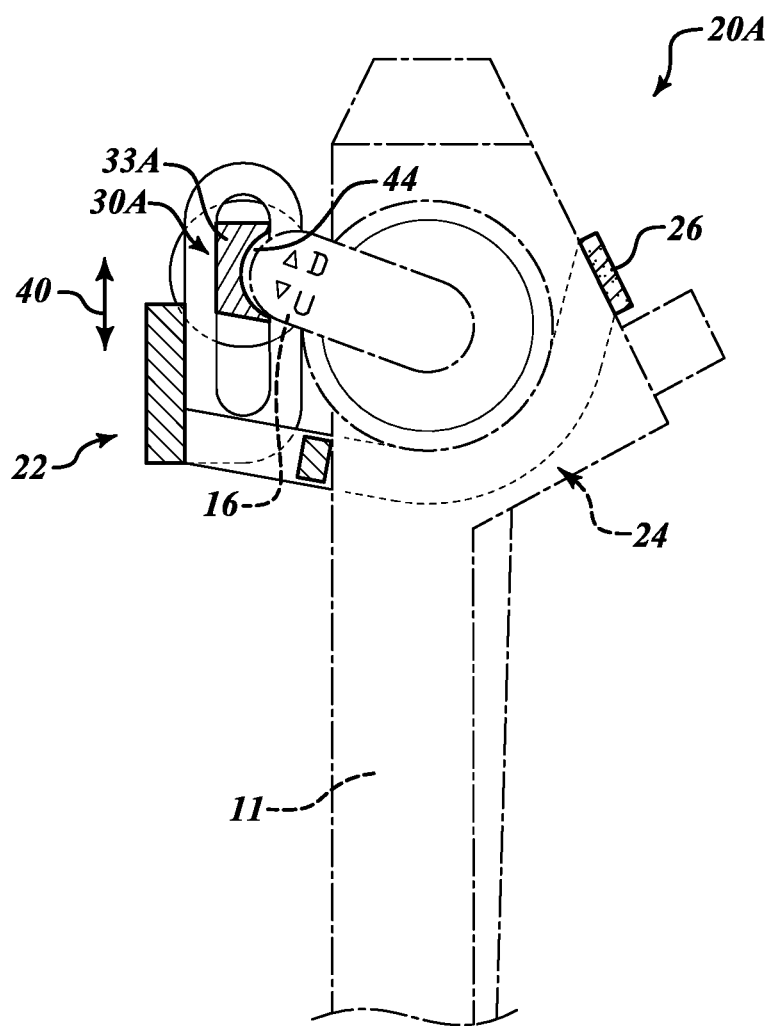
FIG. 6 is a side plan view in partial cutaway of the apparatus of FIG. 3 with an endoscope handle held thereon.

Referring additionally to FIGS. 3 and 6, in some embodiments an apparatus 20A that is shown in FIGS. 3 and 6 can prevent any travel of the angulation lever 16 (shown in phantom in FIG. 6) when the locking mechanism 32 is configured to hold an engagement member 30A in place against the frame 22 (in addition to preventing the angulation lever 16 from returning to a neutral position).

To that end, in some embodiments the engagement member 30A may include a bar member 33A that is configured to prevent any travel of the angulation lever 16—in addition to preventing the angulation lever 16 from returning to a neutral position. In such embodiments, the bar member 33A defines therein a notch 44 that is configured to receive therein the angulation lever 16. It will be appreciated that such embodiments do more than prevent the angulation lever 16 from returning to a neutral position. Instead, such embodiments lock the angulation lever 16 in place and prevent any travel of the angulation lever 16. In such embodiments, not only can the angulation lever 16 not return to a neutral position—but rather, all travel of the angulation lever 16 is prevented.

With the exception of the engagement member 30A, the bar member 33A, and the notch 44, all other details of such embodiments of the apparatus 20A as shown in FIGS. 3 and 6 are similar to those details described above in reference to the apparatus 20 shown in FIGS. 2 and 5 and need not be repeated for an understanding.

Figure 4A:
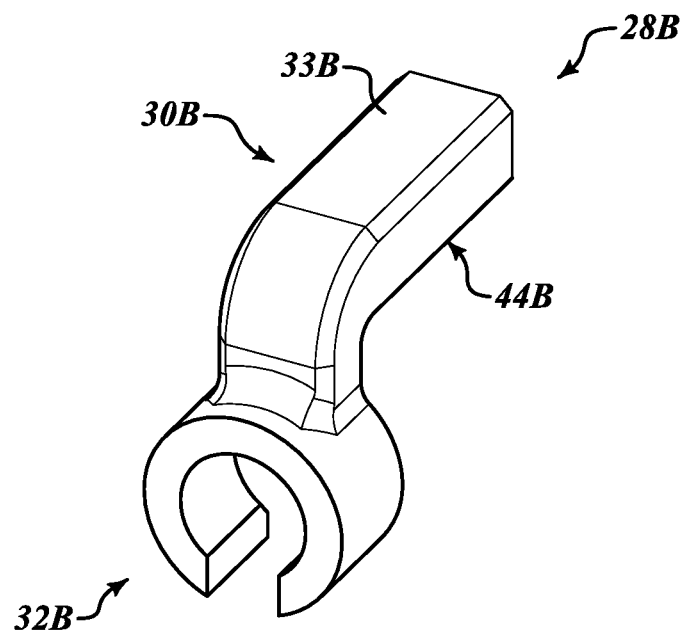
FIGS. 4A and 4B are perspective views of an illustrative angulation lever engagement mechanism.
Figure 4B:
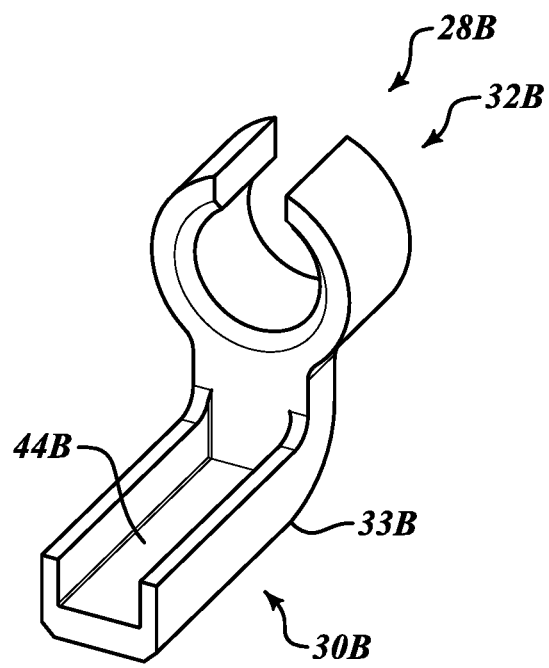
Figure 7:
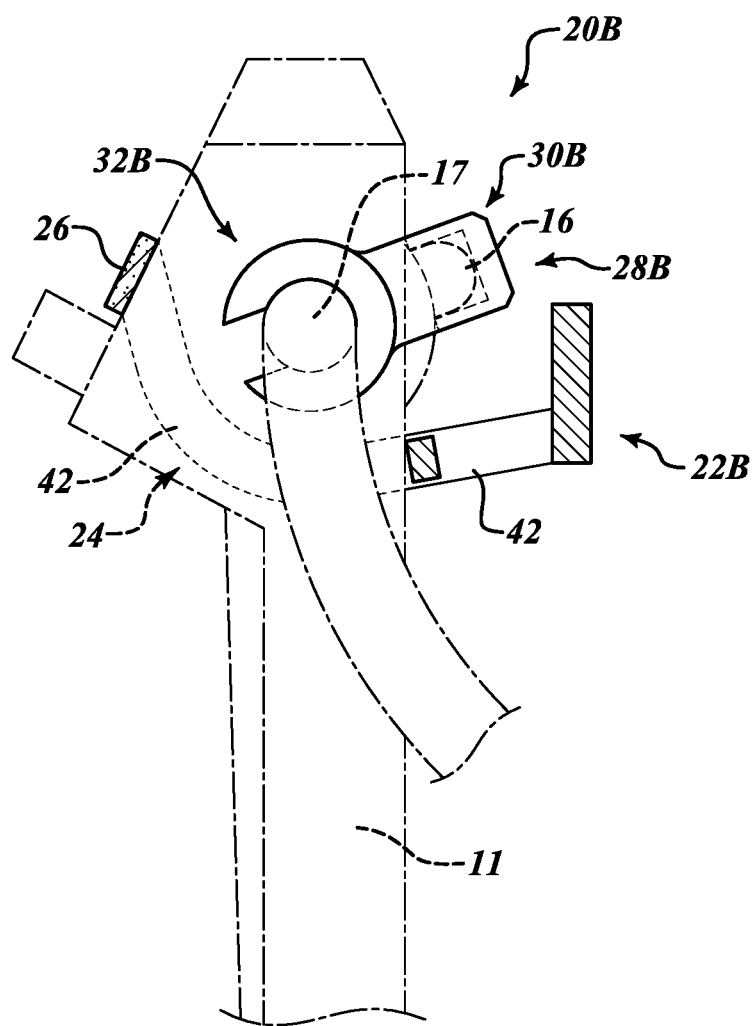
FIG. 7 is a side plan view in partial cutaway of an illustrative apparatus with a frame and support mechanism of FIGS. 2 and 3 with an angulation lever engagement mechanism of FIGS. 4A and 4B.

Referring additionally to FIGS. 4A, 4B, and 7, it will also be appreciated that, in some other embodiments, an apparatus 20B that is shown in FIG. 7 can prevent any travel of the angulation lever 16 (shown in phantom in FIG. 7) when a locking mechanism 33B is integrated with an engagement member 30B and is configured to frictionally engage a portion of the endoscope handle 11 (shown in phantom in FIG. 7).

To that end, in various embodiments the apparatus 20B includes a frame 22B. A support mechanism 24 is attached to the frame 22B and is configured to hold thereon the endoscope handle 11 having the angulation lever 16. The attachment device 26 is configured to hold the endoscope handle 11 in place on the support mechanism 24. An angulation lever engagement mechanism 28B is configured to prevent travel of the angulation lever 16. The angulation lever engagement mechanism 28B includes an engagement member 30B that is configured to receive therein the angulation lever 16 at a position corresponding to a selected deflection of a distal tip (not shown) of the endoscope 10. The angulation lever engagement mechanism 28B also includes a locking mechanism 32B that is configured to lock the engagement member 30B in place. The locking mechanism 32B is integrated with the engagement member 30B and is configured to frictionally engage a portion of the endoscope handle 11.

In various embodiments, the angulation lever engagement mechanism 28B suitably is a one-piece mechanism that includes the engagement member 30B and the locking mechanism 32B. The engagement member 30B includes a bar member 33B that defines therein a notch 44B that is configured to receive therein the angulation lever 16. The locking mechanism 32B is integrated with the engagement member 30B. The locking mechanism 32B includes a ring clip 46 with a slit 48 defined therein.

In various embodiments, a user selects a desired amount of deflection of a distal tip (not shown) of an endoscope with the angulation lever 16 (shown in phantom in FIG. 7). In various embodiments, the ring clip 46 is then placed over the wire bundle 17 (shown in phantom in FIG. 7) via the slit 48. Alternately, if desired a user may first place the ring clip 46 over the wire bundle as described above and then select a desired amount of deflection of a distal tip (not shown) of an endoscope with the angulation lever 16.

In some such embodiments, the ring clip 46 frictionally engages the wire bundle 17 and holds the angulation lever 16 in place. In some other embodiments, a separate ring or bearing may wrap around the wire bundle 17 and the ring clip 46 may rotate about the separate ring or bearing.

It will be appreciated that, in some embodiments, if desired the angulation lever engagement mechanism 28B suitably may be used by itself to lock out an angulation lever of an endoscope handle. That is, in such embodiments, the angulation lever engagement mechanism 28B may be used to lock out an angulation lever of an endoscope handle without the endoscope handle being supported on the support mechanism 24. In other words, if desired a user may lock out an angulation lever 16 with the angulation lever engagement mechanism 28B and may hold the endoscope handle 11 in the user's hand.

It will be appreciated that the various apparatuses disclosed herein may be supported as desired for a particular application. For example, the various apparatuses disclosed herein may be supported on a stand, placed on a flat surface (such as tray or a table top), attached to a lanyard (that is wearable around a user's neck), and the like. However, no limitation is intended regarding ways the apparatuses disclosed herein may be supported.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An angulation lever lock apparatus removably attachable to an endoscope handle, the apparatus comprising:
   a frame including a pair of elongated slots forming lateral sides of the frame and defining a locking axis;
   a support mechanism attached to the frame and configured to removably receive the endoscope handle adjacent to an angulation lever on an external portion of the endoscope handle; and
   an angulation lever engagement mechanism including a central section extending between the pair of elongated slots and end portions slidably engaged and slidably received within respective ones of the pair of elongated slots, the angulation lever engagement mechanism lockable in a position along the lock axis to prevent the angulation lever of the endoscope handle from returning to a neutral position.

2. The apparatus of claim 1, wherein the support mechanism includes at least two support members.

3. The apparatus of claim 1, wherein the angulation lever engagement mechanism includes:
   an engagement member configured to engage the angulation lever of the endoscope handle; and
   a locking mechanism configured to lock the engagement member at a desired position within the pair of elongated slots that corresponds to a selected deflection of a distal tip of an endoscope.

4. The apparatus of claim 3, wherein the engagement member includes a bar member configured to prevent the angulation lever of the endoscope handle from returning to the neutral position.

5. The apparatus of claim 4, wherein the bar member is further configured to abut the angulation lever of the endoscope handle.

6. The apparatus of claim 3, wherein the engagement member includes a bar member configured to prevent travel of the angulation lever of the endoscope handle.

7. The apparatus of claim 6, wherein the bar member defines therein a notch that is configured to receive therein the angulation lever of the endoscope handle.

8. The apparatus of claim 7, wherein the locking mechanism is configured to hold the engagement member in place against the frame.

9. The apparatus of claim 6, wherein the locking mechanism is integrated with the engagement member and is configured to frictionally engage a portion of the endoscope handle.

10. An angulation lever lock apparatus removably attachable to an endoscope handle, the apparatus comprising:
    a frame including at least one elongated slot, wherein the elongated slot includes a first end and a second end that defines allowable locking positions for an angulation lever portion of the endoscope handle;
    a support mechanism attached to the frame and configured to couple around the endoscope handle adjacent to the angulation lever; and
    an angulation lever engagement mechanism configured to prevent the angulation lever of the endoscope handle from returning to a neutral position, the angulation lever engagement mechanism including:
      an engagement member configured to be slidably received within the elongated slot and configured to engage the angulation lever of the endoscope handle at a position corresponding to a selected deflection of a distal tip of an endoscope; and a locking mechanism configured to hold the engagement member in place anywhere from the first end to the second end within the elongated slot.

11. The apparatus of claim 10, wherein the support mechanism includes at least two support members.

12. The apparatus of claim 10, wherein the engagement member includes a bar member configured to prevent the angulation lever of the endoscope handle from returning to the neutral position.

13. The apparatus of claim 12, wherein the bar member is further configured to abut the angulation lever of the endoscope handle.

14. The apparatus of claim 10, wherein the engagement member includes a bar member configured to prevent travel of the angulation lever of the endoscope handle.

15. The apparatus of claim 14, wherein the bar member defines therein a notch that is configured to receive therein the angulation lever of the endoscope handle.

16. An angulation lever lock apparatus removably attachable to an endoscope handle, the apparatus comprising:

a frame including a pair of elongated slots forming the lateral sides of the frame and defining a locking axis;

a support mechanism attached to the frame and configured to removably receive the endoscope handle adjacent to an angulation lever on an external portion of the endoscope handle; and an angulation lever engagement mechanism configured to prevent travel of the angulation lever of the endoscope handle, the angulation lever engagement mechanism including:

an engagement member including a central section extending between the pair of elongated slots and end portions slidably received within respective ones of the pair of elongated slots and configured to receive therein the angulation lever of the endoscope handle at a position corresponding to a selected deflection of a distal tip of an endoscope; and a locking mechanism configured to lock the engagement member in place within the pair of elongated slots, wherein the locking mechanism is integrated with the engagement member.

17. The apparatus of claim 16, wherein the support mechanism includes at least two support members.

18. The apparatus of claim 16, wherein the engagement member includes a bar member that defines therein a notch that is configured to receive therein the angulation lever of the endoscope handle.

19. The apparatus of claim 4, wherein the bar member is slidably receivable within the pair of elongated slots, and wherein the locking mechanism includes:

a stop member attachable to a first end of the bar; and a knob rotatably receivable to a second end of the bar and configured to make contact with an outer surface of a first section the frame including one of the pair of elongated slots and be tightenable to draw the stop member against an outer surface of a second section of the frame including the other one of the pair of elongated slots.

20. The apparatus of claim 10, wherein the locking mechanism includes:

a bar slidably receivable within the elongated slot;

a stop member attachable to a first end of the bar; and a knob rotatably receivable to a second end of the bar and configured to make contact with an outer surface of a first section of the frame including one of the elongated slot and be tightenable to draw the stop member against an outer surface of a second section of the frame, thereby locking the engagement member to the frame anywhere between the first end and the second end of the elongated slot.

* * * * *